(12) United States Patent
Song et al.

(10) Patent No.: US 11,555,906 B2
(45) Date of Patent: Jan. 17, 2023

(54) ULTRASONIC PROBE

(71) Applicant: SAMSUNG MEDISON CO., LTD., Gangwon-do (KR)

(72) Inventors: In Seong Song, Daegu (KR); Jong-sun Ko, Seoul (KR); Yong Jae Kim, Gyeongsangbuk-do (KR); Won Hee Lee, Seoul (KR); Jin Woo Jung, Seoul (KR); Jee Rak Choi, Gyeongsangbuk-do (KR); Yoon Sung Kyung, Gyeonggi-do (KR); Seung Hyun Kim, Gyeonggi-do (KR); Ji Su Kim, Gyeonggi-do (KR); Joong Hyun Park, Seoul (KR); Jin Hwan Park, Seoul (KR); Kyung Min Lee, Gyeonggi-do (KR)

(73) Assignee: SAMSUNG MEDISON CO. LTD., Ganwon-Do (KR)

( * ) Notice: Subject to any disclaimer, the term of this patent is extended or adjusted under 35 U.S.C. 154(b) by 266 days.

(21) Appl. No.: 16/488,365

(22) PCT Filed: Jul. 19, 2017

(86) PCT No.: PCT/KR2017/007782
§ 371 (c)(1),
(2) Date: Aug. 23, 2019

(87) PCT Pub. No.: WO2018/155772
PCT Pub. Date: Aug. 30, 2018

(65) Prior Publication Data
US 2020/0237340 A1    Jul. 30, 2020

(30) Foreign Application Priority Data

Feb. 23, 2017  (KR) .................. 10-2017-0024070

(51) Int. Cl.
*A61B 8/00*        (2006.01)
*G01S 7/52*        (2006.01)

(52) U.S. Cl.
CPC ........ *G01S 7/52047* (2013.01); *A61B 8/4483* (2013.01); *A61B 8/4444* (2013.01)

(58) Field of Classification Search
CPC ... A61B 8/4444; A61B 8/4483; A61B 8/4272; A61B 8/4488; B06B 1/06
See application file for complete search history.

(56) References Cited

U.S. PATENT DOCUMENTS

| 11,231,491 | B2 * | 1/2022 | Scarsella ................ B06B 1/064 |
| 2003/0083573 | A1 | 5/2003 | Azuma et al. |

(Continued)

FOREIGN PATENT DOCUMENTS

| JP | 2003-299196 A | 10/2003 |
| JP | 2005-286701 A | 10/2005 |

(Continued)

OTHER PUBLICATIONS

Search Report issued in corresponding International Application No. PCT/KR2017/007782, dated Nov. 14, 2017.

(Continued)

*Primary Examiner* — Christopher Koharski
*Assistant Examiner* — Taylor Deutsch
(74) *Attorney, Agent, or Firm* — Morgan, Lewis & Bockius LLP

(57) ABSTRACT

An ultrasonic includes: a piezoelectric layer; an absorbing layer disposed at a lower portion of the piezoelectric layer, configured to absorb an acoustic signal; and a connection part disposed between the piezoelectric layer and the absorbing layer. The connection part may deform at least partially so that a plurality of acoustic signals radiated from the piezoelectric layer due to the connection part have different (Continued)

magnitudes. In the case of the ultrasonic probe, since the magnitude of the acoustic energy radiated from the center of the ultrasonic probe is larger than the magnitude of the acoustic energy radiated from the side of the ultrasonic probe, the directivity of the ultrasonic signal is improved and a side lobe is decreased. In addition, an apodization effect capable of suppressing overlapping between adjacent phases can be obtained by using a difference in the magnitude of the acoustic energy to be radiated.

10 Claims, 14 Drawing Sheets

(56) References Cited

U.S. PATENT DOCUMENTS

| | | | |
|---|---|---|---|
| 2003/0189391 A1 | 10/2003 | Shimizu | |
| 2006/0079785 A1 | 4/2006 | Hosono et al. | |
| 2010/0066207 A1* | 3/2010 | Saito | A61B 8/4281 310/335 |
| 2012/0056512 A1 | 3/2012 | Jin et al. | |
| 2013/0150725 A1* | 6/2013 | Choi | A61B 8/4281 600/472 |
| 2013/0241356 A1 | 9/2013 | Kim et al. | |
| 2014/0249419 A1* | 9/2014 | Morita | G10K 11/02 600/459 |
| 2015/0011881 A1* | 1/2015 | Okuda | G10K 11/002 600/443 |
| 2015/0173714 A1* | 6/2015 | Park | B06B 1/0622 600/459 |
| 2017/0113250 A1* | 4/2017 | Lee | A61B 8/4444 |
| 2019/0231310 A1* | 8/2019 | Osawa | A61B 8/4444 |

FOREIGN PATENT DOCUMENTS

| | | |
|---|---|---|
| JP | 4338568 B2 | 10/2009 |
| JP | 2011-146764 A | 7/2011 |
| KR | 10-2015-0020945 A | 2/2015 |

OTHER PUBLICATIONS

Extended European Search Report dated Jan. 22, 2020 issued in European Patent Application No. 17898243.5.
Communication pursuant to Article 94(3) EPC dated Apr. 20, 2022 issued in European Patent Application No. 17898243.5.

* cited by examiner (a) Linear (b) Convex (c) Micro convex (d) 2D Matrix (a)

(b)

(c)

(d)

<CHANGE OF ENERGY RADIATED DEPENDING ON POSITION>

(a) BEAM PATTERN OF DISCLOSURE (b) BEAM PATTERN OF RELATED ART (a)

(b)

(c)

(d)

(a)

(b)

(c)

(d)

(a)

(c)

(e)

ULTRASONIC PROBE

CROSS-REFERENCE OF RELATED APPLICATIONS

This application is the U.S. National Phase under 35 U.S.C. § 371 of International Patent Application No. PCT/KR2017/007782, filed on Jul. 19, 2017, which in turn claims the benefit of Korean Patent Application No. 10-2017-0024070, filed Feb. 23, 2017, the entire disclosures of which applications are incorporated by reference herein.

TECHNICAL FIELD

The disclosure relates to an ultrasonic probe, and more particularly, to a technology for modifying a shape of a connection part of the ultrasonic probe to radiate acoustic energy radiated from the ultrasonic probe to different magnitudes depending on positions.

BACKGROUND ART

An ultrasonic diagnostic apparatus may refer to an apparatus configured to irradiate ultrasonic signals to a target part inside of an object and receive ultrasonic signals, which are reflected from the object (echo ultrasonic signals), thereby noninvasively acquiring images about soft tissue layer or blood vessels by using information thereon.

The ultrasonic diagnostic apparatus is relatively compact and inexpensive in comparison with another type of diagnostic imaging apparatus, e.g., X-ray device, Computerized Tomography Scanner (CT), Magnetic Resonance Image (MRI), diagnostic nuclear medical apparatus. In addition, the ultrasonic diagnostic apparatus is capable of obtaining an image about the inside of the object in real time, and the ultrasonic diagnostic apparatus is safe because there is no risk of radiation exposure. Therefore, the ultrasonic diagnostic apparatus is widely used in medical examination at cardiology, abdomen, urology, and maternity clinics.

Therefore, the ultrasonic diagnostic apparatus includes an ultrasound probe configured to transmit ultrasonic signals to an object and receive response signals reflected from the object so as to acquire an ultrasound image of the inside of the object.

The ultrasound probe includes a piezoelectric layer in which a piezoelectric material in the ultrasound probe vibrates and converts an electrical signal into an acoustic signal, a matching layer configured to allow ultrasonic waves, which is generated in the piezoelectric layer, to be effectively transmitted to an object by reducing a difference in acoustic impedance between the piezoelectric layer and the object, lens configured to focus ultrasonic waves, which move to the front side of the piezoelectric layer, to a particular point, an absorbing layer configured to prevent the ultrasonic waves from moving to the rear side of the piezoelectric layer or prevent the image distortion by reflecting the ultrasonic waves, and a connection part electrically connected to the absorbing layer and the piezoelectric material.

In general, an acoustic element of the ultrasonic probe has a structure in which a plurality of materials are stacked in a rectangular shape. In this case, a manufacturing method is simple due to a single shape, but the characteristics of the ultrasonic probe are consistently problematic. That is, there is a problem that the directivity of the ultrasonic signal decreases and a side lobe increases because the magnitude of acoustic energy radiated from the center of the ultrasonic probe is equal to the magnitude of the acoustic energy radiated from the side.

DISCLOSURE

Technical Problem

In order to solve the above-described problems, the disclosure is to provide an ultrasonic probe in which the magnitude of acoustic energy radiated from the ultrasonic probe is increased at the center and decreased at the side, thereby improving the directivity of an ultrasonic signal.

Technical Solution

One aspect of the disclosure provides an ultrasonic probe including: a piezoelectric layer; an absorbing layer disposed at a lower portion of the piezoelectric layer, configured to absorb an acoustic signal; and a connection part disposed between the piezoelectric layer and the absorbing layer. The connection part may deform at least partially so that a plurality of acoustic signals radiated from the piezoelectric layer due to the connection part have different magnitudes.

The connection part may have a symmetrical shape with respect to a center line of the connection part.

At least one side of the connection part may have a curved shape.

At least one side of the connection part may have an inwardly recessed shape.

An outer circumferential surface of the connection part may have a convex shape symmetrically.

An outer circumferential surface of the connection part may have a concave shape symmetrically.

The width of the connection part may have a different width from one side of the connection part to the center of the connection part.

The width of the connection part may linearly increase or increase in a curved shape from one side of the connection part to the center of the connection part.

The width of the connection part may linearly decrease or decrease in a curved shape from one side of the connection part to the center of the connection part.

The connection part may deform partially so that a magnitude of an acoustic signal radiated by the piezoelectric layer linearly increases or increase in a curved shape from one side of the connection part to the center of the connection part.

The connection part may deform partially so that a magnitude of an acoustic signal radiated by the piezoelectric layer linearly decreases or decrease in a curved shape from one side of the connection part to the center of the connection part.

The connection part may have the form of a circle, an ellipse or a rhombus.

The connection part may include at least one flexible printed circuit board (PCB).

The connection part may include a conductive material.

The connection part may be electrically connected to the piezoelectric layer.

The connection part may include a plurality of connection layers. An insulating layer is disposed between the connection layers.

The connection part may include a first connection part and a second connection part. An insulating layer is disposed between the first connection part and the second connection part.

An outer circumferential surface of the first connection part may have a convex shape or a concave shape symmetrically.

An outer circumferential surface of the second connection part may have a convex shape or a concave shape symmetrically.

The ultrasonic probe may further include the insulating layer disposed at the lower portion of the connection part.

Advantageous Effects

According to the above-described ultrasonic probe, since the magnitude of the acoustic energy radiated from the center of the ultrasonic probe is larger than the magnitude of the acoustic energy radiated from the side of the ultrasonic probe, the directivity of the ultrasonic signal is improved and a side lobe is decreased.

In addition, an apodization effect capable of suppressing overlapping between adjacent phases can be obtained by using a difference in the magnitude of the acoustic energy to be radiated.

MODES OF THE INVENTION

Embodiments described herein and configurations illustrated in the accompanying drawings are only certain examples of the disclosure, and various modifications may be made at the time of filing of the present application to replace the embodiments and drawings of the present specification.

In addition, terms used herein are intended to only describe certain embodiments, and shall by no means restrict and/or limit the disclosure. Unless clearly used otherwise, expressions in a singular form include the meaning in a plural form.

In the present specification, terms such as "comprising," "having" or "including" are intended to designate the presence of characteristics, numbers, steps, operations, elements, parts or combinations thereof, and shall not be construed to preclude any possibility of presence or addition of one or more other characteristics, numbers, steps, operations, elements, parts or combinations thereof.

In addition, although terms including ordinal numbers such as "first" or "second" may be used herein to describe various elements, the elements should not be limited by such terms.

Hereinafter, embodiments of the disclosure will now be described in detail with reference to the accompanying drawings to be readily practiced by a person of ordinary skill in the art.

Figure 1:
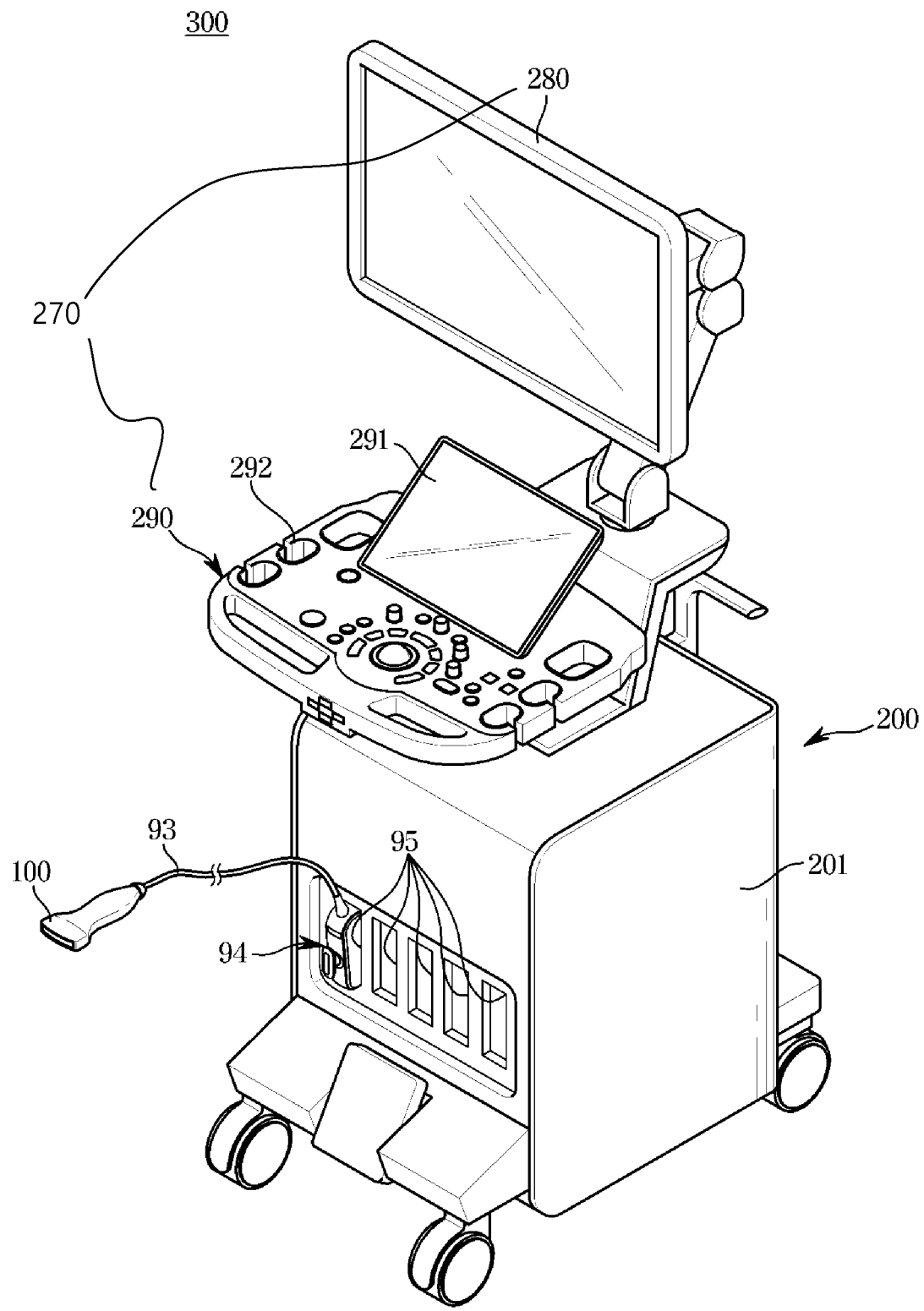
FIG. 1 is a perspective view illustrating an exterior of an ultrasonic diagnostic apparatus according to an embodiment of the disclosure.
Figure 2:
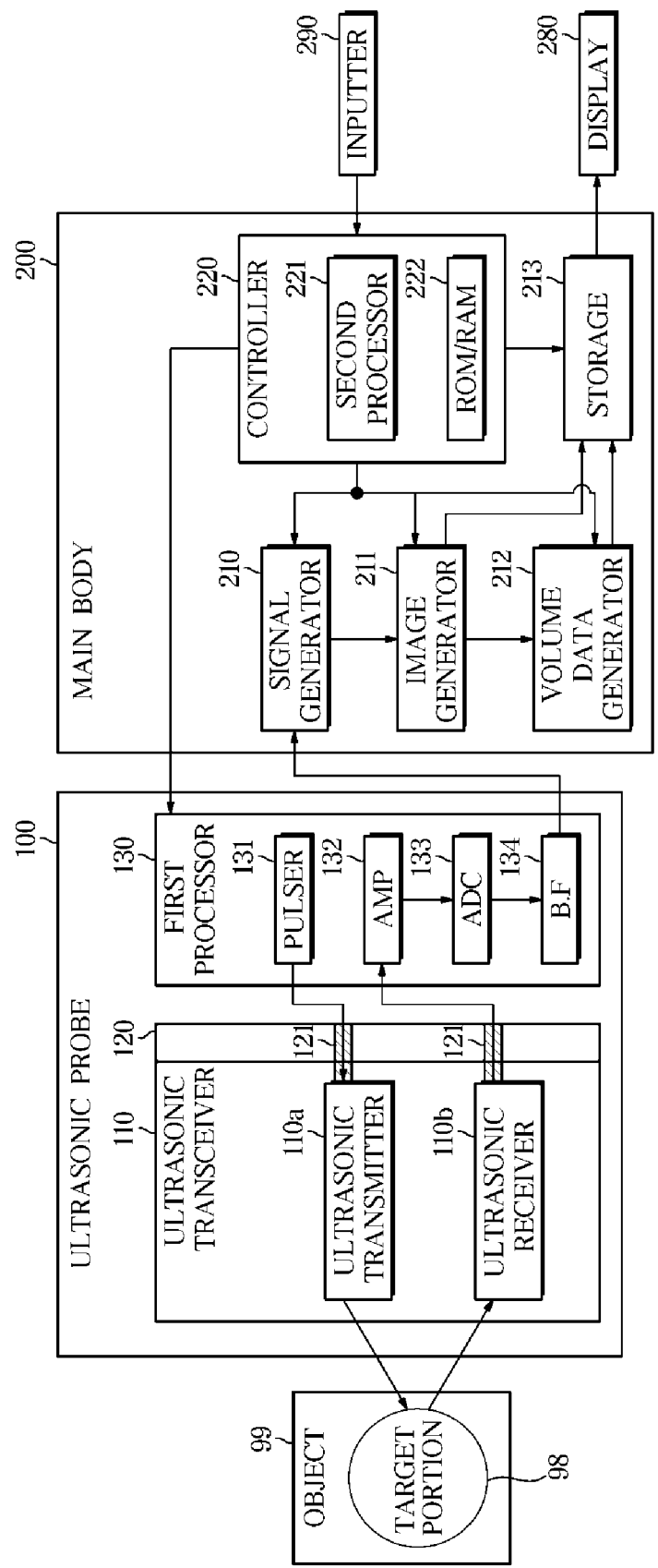
FIG. 2 is a block diagram illustrating an internal configuration of an ultrasonic diagnostic apparatus according to an embodiment of the disclosure.
Figure 3:
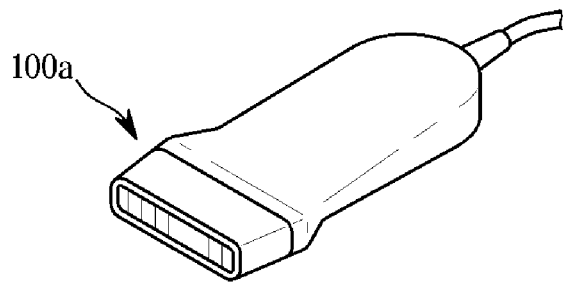
FIG. 3 is a perspective view illustrating exteriors of various types of ultrasonic probes according to an embodiment of the disclosure.
Figure 3:
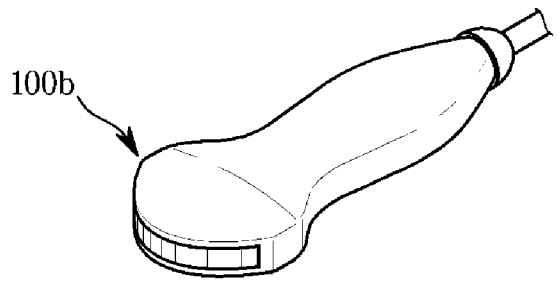
Figure 3:
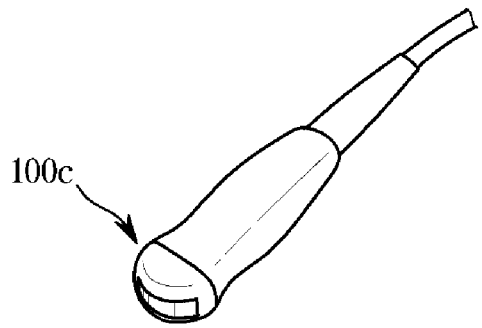
Figure 3:
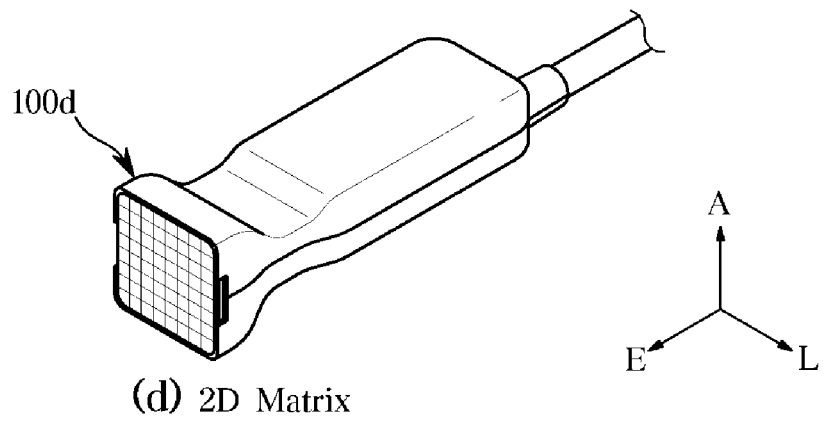

FIG. 1 is a perspective view of an ultrasonic diagnostic apparatus 300 with an ultrasonic probe 100, according to an embodiment of the disclosure, FIG. 2 is a block diagram for describing elements of the ultrasonic diagnostic apparatus 300, and FIG. 3 illustrates exteriors of various types of ultrasonic probes 100a to 100d classified according to the shapes of transducers of the ultrasonic probe 100.

Referring to FIGS. 1 and 2, the ultrasonic diagnostic apparatus 300 may include a main body 200, an inputter 290 for receiving instructions from a user to control the ultrasonic diagnostic apparatus 300, and a display 280 for outputting information received from the inputter 290 and the main body 200.

Particularly, the main body 200 may control general operation of the ultrasonic diagnostic apparatus 300, and accordingly, may be equipped with various parts to control overall operation of the ultrasonic probe 100 or the main body 200. The main body 200 and the ultrasonic probe 100 may transmit data to or receive data from each other using a connection cable 93 or a wireless communication module.

As illustrated in FIG. 1, the ultrasound probe 100 and the main body 200 may be connected to be able to communicate with each other using the connection cable 93. An electrical signal output from the ultrasonic probe 100 may be transmitted to the main body 200 through the connection cable 93. A control command generated by the main body 200 may also be transmitted to the ultrasonic probe 100 through the connection cable 93.

A connector 94 may be provided on one end of the connection cable 93. The connector 94 may be connected to or disconnected from a port 95 provided on an outer case 201 of the main body 200. When the connector 94 is connected to the port 95, the ultrasonic probe 100 and the main body 200 may be communicatively connected.

A probe holder 292 may be provided on one side surface of the main body 200 to hold the ultrasonic probe 100 therewith. A number of probe holders 292 may correspond to the number of ultrasonic probes 100. The probe holder 292 may be attached to or detached from the main body 200. When the ultrasonic probe 100 is not in use, a user may store the ultrasonic probe 100 by holding the ultrasonic probe 100 with the probe holder 292.

Furthermore, the main body 200 may receive the electrical signal output from the ultrasonic probe 100 and transmit the electrical signal generated by the main body 200 to the ultrasonic probe 100 through a wireless communication network. In this case, a wireless communication module including an antenna and a wireless communication chip may be installed in each of the ultrasonic probe 100 and the main body 200.

The wireless communication module may be a short-range wireless communication module using at least one among Bluetooth™, Bluetooth™ low energy, infrared data association (IrDA), wireless fidelity (Wi-Fi), Wi-Fi Direct, Ultra-Wide Band (UWB), and Near Field Communication (NFC), or may be a wireless communication module supporting a 3GPP family, 3GPP2 family, or IEEE family wireless communication network authenticated by the International Telecommunication Unit (ITU).

The main body 200 may exchange data with a server of a hospital or another medical device in the hospital connected to the main body 200 through a medical image information system (a picture archiving and communication system (PACS)) through a communicator. The main body 200 may exchange data according to digital imaging and communications in medicine (DICOM) standards. However, embodiments are not limited thereto.

The display 280 may be coupled to the main body 200 and output various information received from the main body 200.

Particularly, the display 280 may display an ultrasonic image of a target inner portion of an object. The ultrasonic image displayed on the display 280 may be a two-dimensional (2D) ultrasonic image or a three-dimensional (3D) ultrasonic image. Various ultrasonic images may be displayed on the display 280 according to an operating mode of the ultrasonic diagnostic apparatus 300.

In embodiments, examples of the ultrasonic image include an amplitude mode (A-mode) image, a brightness mode (B-Mode) image, a motion mode (M-mode) image, a color mode (C-mode) image, and a Doppler mode (D-mode) image.

As used herein, the A-mode image may refer to an ultrasonic image representing the magnitude of an ultrasonic signal corresponding to an echo ultrasonic signal, the B-mode image may refer to an ultrasonic image representing the magnitude of the ultrasonic signal corresponding to the echo ultrasonic signal using brightness, and the M-mode image may refer to an ultrasonic image representing motion of an object at a specific location according to time. The D-mode image may refer to an ultrasonic image representing a moving object in the form of waveforms according to the Doppler effect. The C-mode image may refer to an ultrasonic image representing a moving object in the form of color spectrums.

Accordingly, the display 280 may be implemented as well-known various displays, such as a cathode ray tube (CRT), a liquid crystal display (LCD), a light-emitting diode (LED), a plasma display panel (PDP), an organic light-emitting diode (OLED), etc.

The inputter 290 may be implemented in various ways, e.g., as a keyboard, a foot switch, or a foot pedal.

For example, the keyboard may be implemented in hardware. In this case, the keyboard may include at least one among a switch, a key, a joystick, and a track ball. Alternatively, the keyboard may be implemented by software, e.g., as a graphical user interface (GUI). In this case, the keyboard may be displayed on the display 280.

In a case that the display 280 is implemented in a type of touch screen, the display 280 may also serve as the inputter 290. That is, the main body 200 may receive various commands from the user through at least one of the display 280 and the inputter 290. In embodiments, a third display 291 illustrated in FIG. 1 may have both display and input functions.

The display 280 and the inputter 290 may be defined together as an input/output (I/O) device 270 since they may receive information from the user or transmit information to the user.

Referring to FIG. 2, the ultrasonic probe 100 may include an ultrasonic transceiver 110 configured to generate or receive ultrasonic waves, and a first processor 130 which is electrically connected to the ultrasonic transceiver 110 and controls an operation of the ultrasonic transceiver 110 or performs signal processing using an electrical signal output from an ultrasonic element.

The ultrasonic transceiver 110 may include an ultrasonic transducer which may generate ultrasonic waves or an electrical signal corresponding to the ultrasonic waves.

The ultrasonic transducer may generate ultrasonic waves by converting alternating-current (AC) energy of a predetermined frequency into mechanical vibration of the predetermined frequency or convert mechanical vibration of a predetermined frequency based on received ultrasonic waves into AC energy. Thus, the ultrasonic transducer may generate ultrasonic waves or output an electrical signal corresponding to receive ultrasonic wave.

Referring to the embodiment of FIG. 2, the ultrasonic transceiver 110 may include an ultrasonic transmitter 110*a* and an ultrasonic receiver 110*b*.

The ultrasonic transmitter 110*a* may generate ultrasonic waves of a frequency corresponding to a frequency of a pulse signal according to the pulse signal transmitted by the first processor 130 or a second processor 221. The generated ultrasonic waves may be emitted to a target portion 98 of an object 99.

The ultrasonic receiver 110*b* may receive ultrasonic waves reflected from the target portion 98 of the object 99 or generated from the target portion 98 by laser or the like, and convert a received signal into an ultrasonic signal. The ultrasonic receiver 110*b* may include a plurality of ultrasonic transducers. The ultrasonic transducers respectively output ultrasonic signals. Thus, the ultrasonic receiver 110*b* may output ultrasonic signals of a plurality of channels.

The ultrasonic transceiver 110 may be installed on a surface of an acoustic absorber 120. The acoustic absorber 120 may include a first connection part 121 corresponding to the ultrasonic transceiver 110.

In embodiments, the first connection part 121 may be installed in the acoustic absorber 120 to pass through the acoustic absorber 120. In this case, the first connection part 121 may penetrate from one surface of the acoustic absorber 120 to another surface thereof.

The first processor 130 may generate and output an electrical signal for controlling the ultrasonic transceiver 110, or perform various signal processing using an ultrasonic signal transmitted from the ultrasonic transceiver 110.

The electrical signal output from the first processor 130 may be transmitted to the ultrasonic transceiver 110, for example, the ultrasonic transmitter 110*a*, through the first connection part 121. The ultrasonic transmitter 110*a* may be driven by the electrical signal transmitted thereto.

According to the embodiment of FIG. 2, the first processor 130 may include at least one among a pulser 131, an amplifier (AMP) 132, an analog-to-digital converter (ADC) 133, and a beamformer (BF) 134.

The pulser 131 may generate a voltage of a predetermined frequency for driving the ultrasonic transceiver 110, and transmit the voltage to the ultrasonic transceiver 110. The ultrasonic transceiver 110 may vibrate according to the amplitude and frequency of the voltage output from the pulser 131 to generate ultrasonic waves.

The frequency and amplitude of the ultrasonic waves generated by ultrasonic transceiver 110 may be determined by the amplitude and frequency of the voltage generated by the pulser 131. The voltage output from the pulser 131 may be applied to the ultrasonic transceiver 110 after a predetermined time. Thus, the ultrasonic waves generated by the ultrasonic transceiver 110 may be concentrated on the target portion 98 or be steered in a predetermined direction.

In embodiments, the pulser 131 may be included in the second processor 221. In this case, the first processor 130 may not include the pulser 131.

The AMP 132 may amplify an ultrasonic signal output from the ultrasonic receiver 110b of the ultrasonic transceiver 110. In one embodiment, the AMP 132 may differently amplify ultrasonic signals of a plurality of channels output from a plurality of ultrasonic transceivers 110, thereby compensating for the differences between the intensities of the ultrasonic signals of the plurality of channels.

When the amplified ultrasonic signal is an analog signal, the ADC 133 may convert the amplified ultrasonic signal into a digital signal. The ADC 133 may output a digital signal by sampling the ultrasonic signal which is an analog signal at a predetermined sampling ratio.

The BF 134 may concentrate ultrasonic signals input via a plurality of channels. The BF 134 may generate a beamformed signal by concentrating a signal transmitted from the ultrasonic transceiver 110, the AMP 132, or the ADC 133. The BF 134 may perform electronic-beam scanning, steering, concentrating, apodizing, and a calibration function on signals of a plurality of channels.

When the ultrasonic probe 100 is a wireless ultrasonic probe, a battery (not shown) which supplies power to the ultrasonic probe 100 may be further provided.

As illustrated in FIG. 2, the main body 200 may include a signal generator 210, an image generator 211, a volume data generator 212, a storage 213, a ROM/RANI 222, and a controller 220.

The signal generator 210 may perform various signal processing on the beamformed signal. For example, the signal generator 210 may perform at least one of a filtering process, a detection process, and a compression process. The filtering process is a process to eliminate other signals than a signal in a particular bandwidth by applying a filter to the beamformed signal. The filtering process may include a harmonic imaging process to eliminate fundamental frequency components while passing harmonic signals. The detection process is a process to transform the voltage of an ultrasound signal from a radio frequency format to a video signal format. The compression process is a process to reduce the difference in amplitude between ultrasound signals. The signal generator 210 may be omitted as needed.

The image generator 211 may convert the beamformed signal or the signal processed by the signal processor 210 to an ultrasound image in the format of a still image or moving image, and if necessary, may process image processing on the still image or the moving image.

The image generator 211 may generate an ultrasound image using scan conversion. The ultrasound image may include an A mode image, a B mode image, an M mode image, a D mode image, or a 3D image. The ultrasound image may include the D image formed by using the Doppler effect.

The A mode ultrasound image may refer to an ultrasound image obtained by imaging the intensity of reflection in amplitudes based on a distance or time between the target portion 98 and the ultrasonic probe 100, and the B mode ultrasound image refers to an ultrasound image obtained by representing the intensity of the ultrasound by brightness.

The M mode ultrasound image may refer to an ultrasound image obtained by imaging an extent of change in motion of the object being imaged. The D image may include a bloodstream Doppler image (also referred to as a color Doppler image), a tissue Doppler image that represents movement of tissues, or a spectral Doppler image that represents the moving speed of the object in a waveform.

The image generator 211 may also correct the generated ultrasound image. For example, the image generator 211 may correct brightness, luminosity, sharpness, contrast, color or the like of an entire or a part of the ultrasound image in order for the user to clearly view tissues in the ultrasound image. As necessary, the image 230 generator 211 may cancel noise in the ultrasound image or perform pixel interpolation.

The image generator 211 may transmit the generated or corrected ultrasound image to the storage 213, or display the ultrasound image on the display 280. The image generator 211 may also transmit the generated or corrected ultrasound image to the volume data generator 212 to obtain ultrasound volume data.

The volume data generator 212 may obtain ultrasound volume data representing a 3D volume based on the generated or corrected 2D ultrasound image.

The signal generator 210, the image generator 211, and the volume data generator 212 may be implemented by a central processing unit (CPU) or a graphic processing unit (GPU). The CPU or GPU may be implemented with at least one semiconductor chip and associated components.

The storage 213 may store various programs or data related to functions of the controller 220, ultrasound images, and various kinds of information regarding the ultrasound images. The storage 213 may be implemented using a semiconductor storage device, a magnetic disk storage device, or a magnetic tape storage device.

The controller 220 may control overall operations of the ultrasound diagnostic apparatus 300 in accordance with commands from the user or predefined settings. For example, the controller 220 may generate a control command based on the frequency of an ultrasound to be irradiated, and transmit the control command to the pulser 131 of the first processor 130, which may in turn, apply a voltage with a certain frequency to the ultrasonic transceiver 110 according to the control command. Accordingly, the ultrasonic transceiver 110 may generate and irradiate an ultrasound with the certain frequency to the target portion 98 of the object 99.

The controller 220 may include a read only memory (ROM) or random access memory (RAM) to assist in the second processor 221 and operation of the second processor 221. The second processor 221 may be implemented by a CPU. The CPU may be implemented with one or more semiconductor chips and associated components.

FIG. 3 illustrates the exteriors of various types of ultrasonic probes 100 classified according to a shape of the ultrasonic transceiver 110.

An ultrasonic probe 100a illustrated in FIG. 3A is a linear probe in which transducers are arranged in a straight line.

An ultrasonic probe 100*b* illustrated in FIG. 3B is a convex ultrasonic probe which has a convex surface and thus through which a fan-shape image is generated. The ultrasonic probe 100*b* is mainly used to check a large area, such as the abdomen. A basic principle of operating the ultrasonic probe 100*b* is the same as that of operating the ultrasonic probe 100*a* which is a linear probe.

An ultrasonic probe 100*c* illustrated in FIG. 3C is a micro-convex ultrasonic probe having the effect of a convex ultrasonic probe and designed to have a small size to easily inspect a narrow part of the object 99.

An ultrasonic probe 100*d* illustrated in FIG. 3D is a 2D matrix-array ultrasonic probe capable of providing a 3D ultrasonic diagnostic image which provides a 360° 3D image of the object 99 in real time.

However, embodiments are not limited thereto, and the ultrasonic probe 100 may be another type of a probe well known in this art, such as a phased array probe or a 3D matrix probe, other than those illustrated in FIG. 3. The structure of the ultrasonic probe 100 to be described later may be employed as the structure of any type of the ultrasonic probe 100 described above, and the characteristics of the ultrasonic probe 100 described later may be applied to all types of the ultrasonic probes 100 described above.

External and internal configurations of the ultrasonic probe 100 and the ultrasonic diagnostic apparatus 300 have thus far been described. An internal laminated structure of an acoustic element of the ultrasonic probe 100 will now be described.

Figure 4:
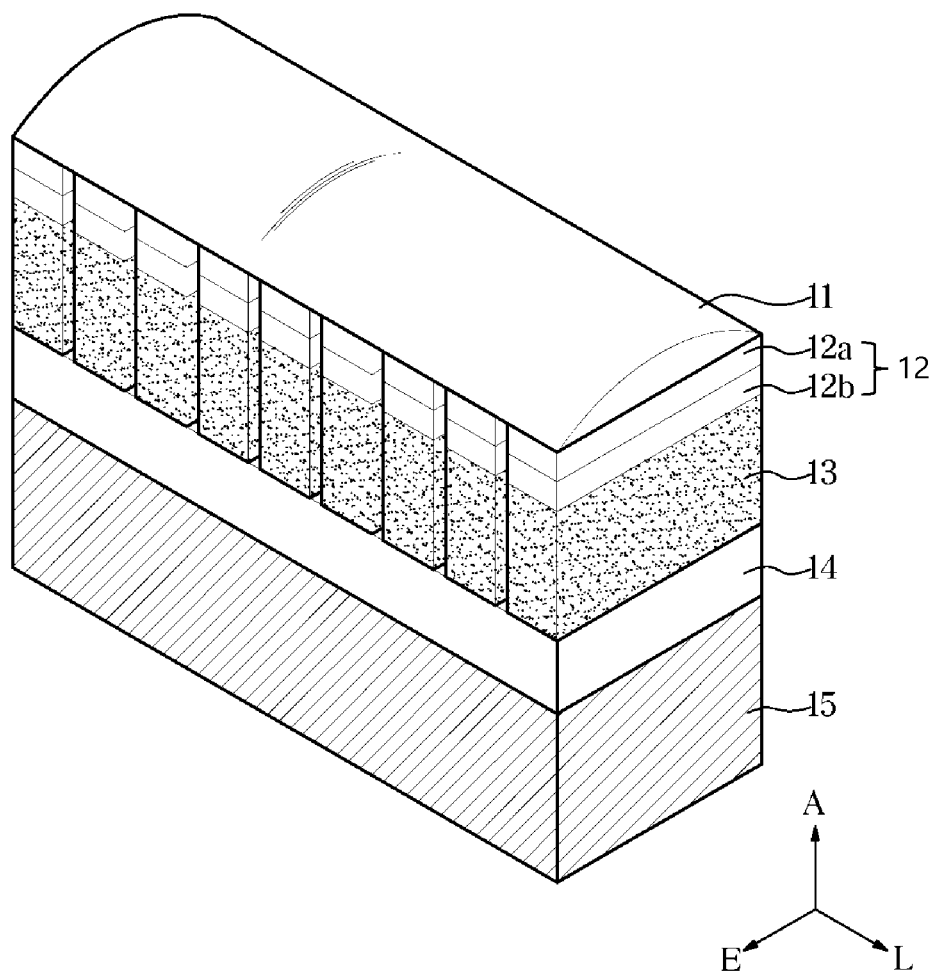
FIG. 4 is a view illustrating a laminated structure of an acoustic element of an ultrasonic probe according to a related art.

FIG. 4 is a view illustrating a laminated structure of an acoustic element of an ultrasonic probe according to a related art.

Referring to FIG. 4, the acoustic element of the ultrasonic probe may include a piezoelectric layer 13, a matching layer 12 disposed at an upper portion of the piezoelectric layer 13, an acoustic lens 11 disposed at the upper portion of the matching layer 12, an absorbing layer 15 disposed at a lower portion of the piezoelectric layer 13, a connection portion 14 disposed between the piezoelectric layer 13 and the absorbing layer 15, and the like.

Particularly, the piezoelectric layer 13 may include a piezoelectric material, and the piezoelectric material vibrates and converts between electric signals and acoustic signals. Although not illustrated in the drawings, electrodes for connecting the electrical signals may be formed on the upper and lower portions of the piezoelectric layer 13.

The matching layer 12 may reduce an acoustic impedance difference between the piezoelectric layer 13 and the object 99 so that the ultrasonic waves emitted from the piezoelectric layer 13 can be effectively transmitted to the object 99. The matching layer 12 may be formed a single layer, or formed of a first matching layer 12*a* and a second matching layer 12*b* as illustrated in FIG. 4.

The absorbing layer 15 may serve to block or absorb the ultrasonic signal from propagating toward the rear of the ultrasonic probe, or to reflect the ultrasonic waves so as to prevent distortion of an image. The absorbing layer 15 may focus a transmitted ultrasonic signal to a predetermined position in an elevation direction of the ultrasonic probe.

In the case of the ultrasonic probe according to the related art, as illustrated in FIG. 4, all the materials constituting the acoustic element are laminated by the same model. In such a structure, a method of manufacturing the ultrasonic probe is easy, while the characteristics of the ultrasonic probe are consistently problematic.

That is, due to the same model, there is a problem that the directivity of the ultrasonic signal decreases and a side lobe increases because the magnitude of the acoustic energy radiated from the center of the ultrasonic probe is equal to the magnitude of the acoustic energy radiated from the side.

However, in the case of the ultrasonic probe 100 according to the disclosure, since the structure of the connection part 50 is partially modified, the magnitude of the acoustic energy radiated from the center of the ultrasonic probe 100 is larger than the magnitude of the acoustic energy radiated from the side of the ultrasonic probe 100. Therefore, there is an effect that the directivity of the ultrasonic signal is improved and the side lobe of the ultrasonic probe 100 is decreased. Hereinafter, the structure of the disclosure will be described with reference to the drawings.

Figure 5:
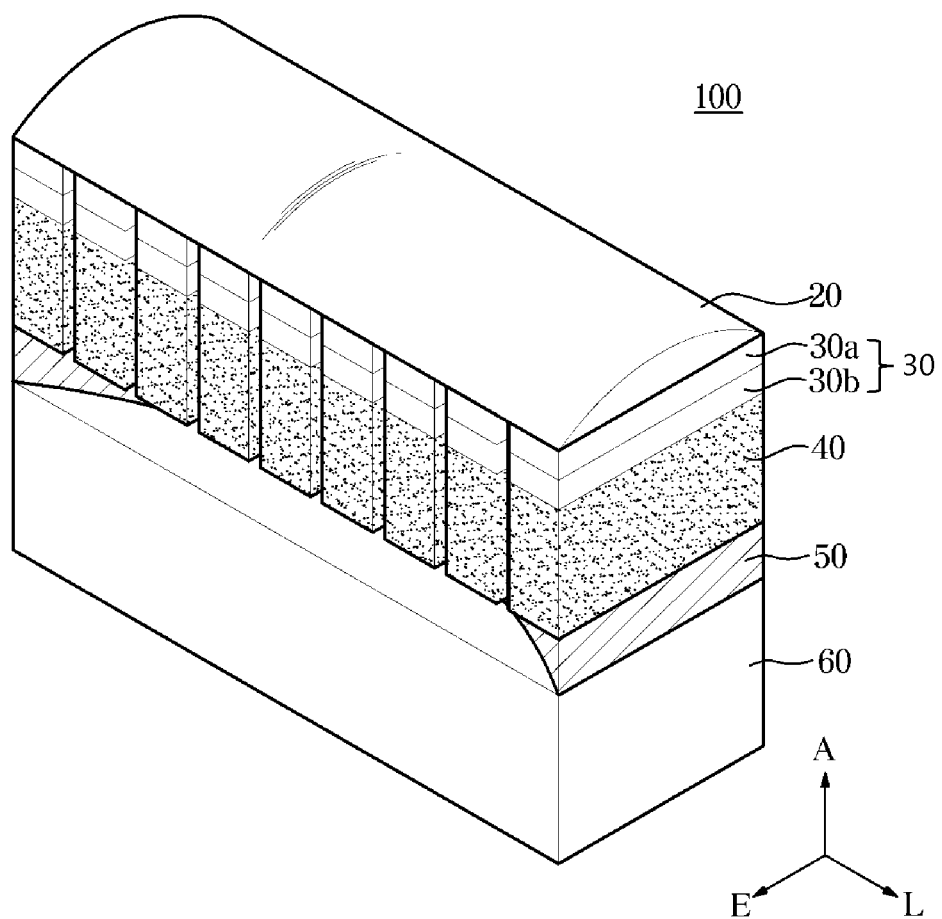
FIG. 5 is a view illustrating a laminated structure of an acoustic element of an ultrasonic probe according to an embodiment of the disclosure.
Figure 6:
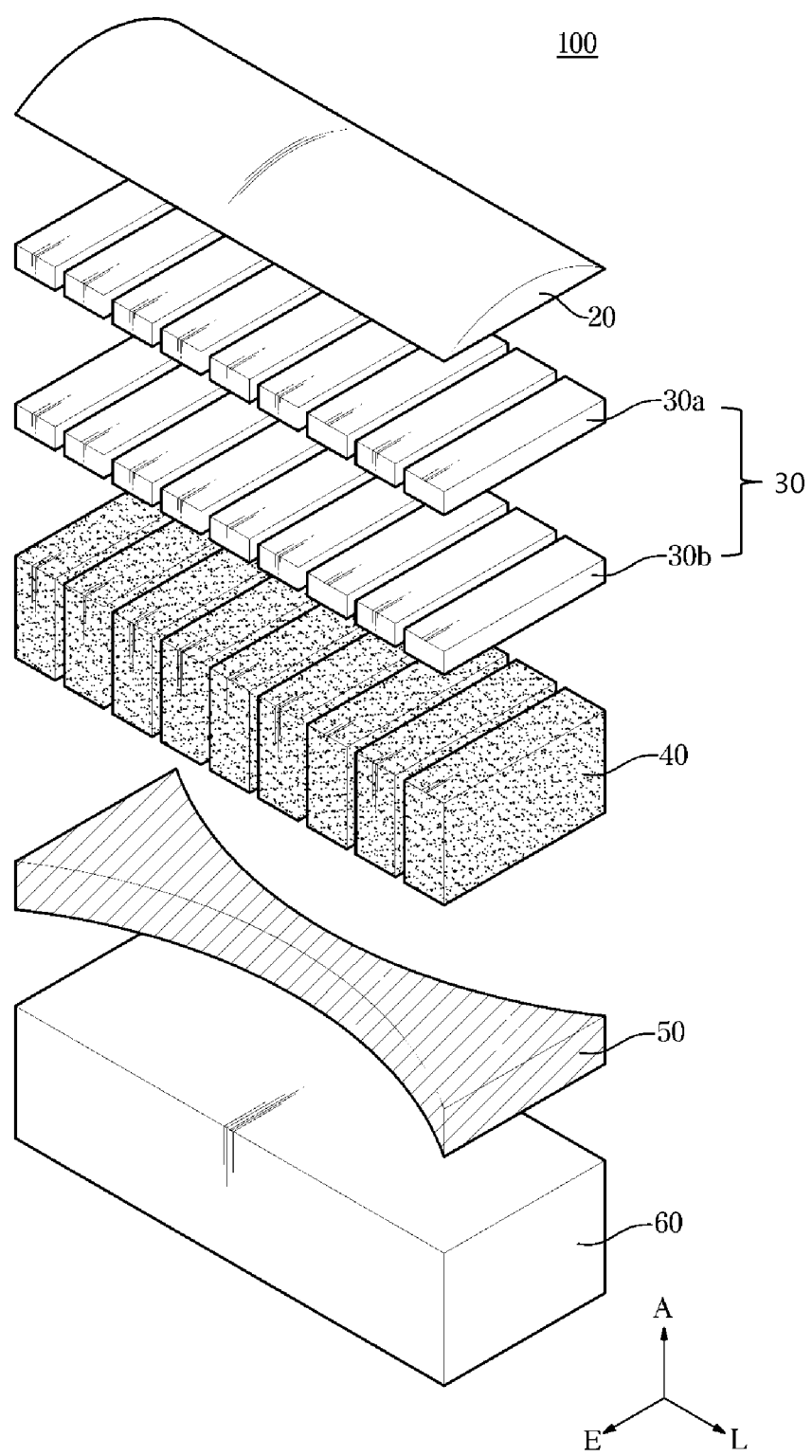
FIG. 6 is an exploded perspective view illustrating an acoustic element of an ultrasonic probe according to an embodiment of the disclosure.
Figure 7:
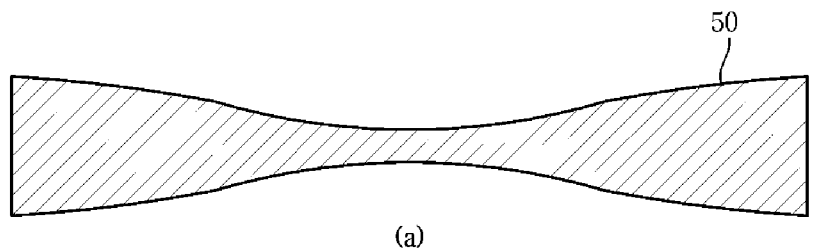
FIGS. 7 and 8 are views illustrating the magnitude of acoustic energy radiated differently depending on a position of a connection part according to an embodiment of the disclosure.
Figure 7:
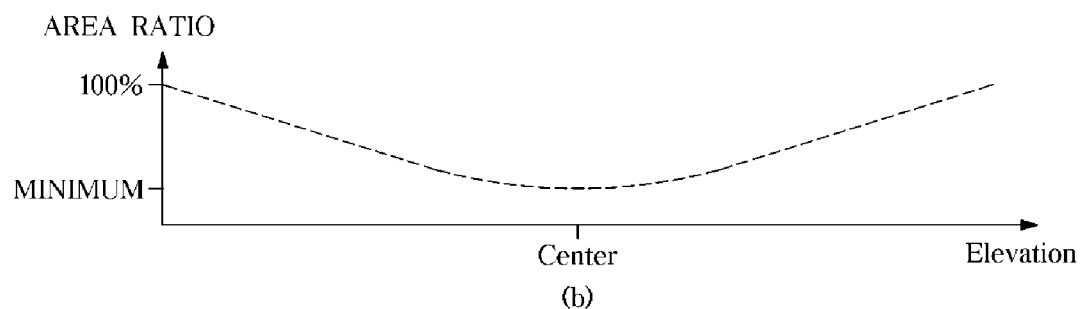
Figure 7:
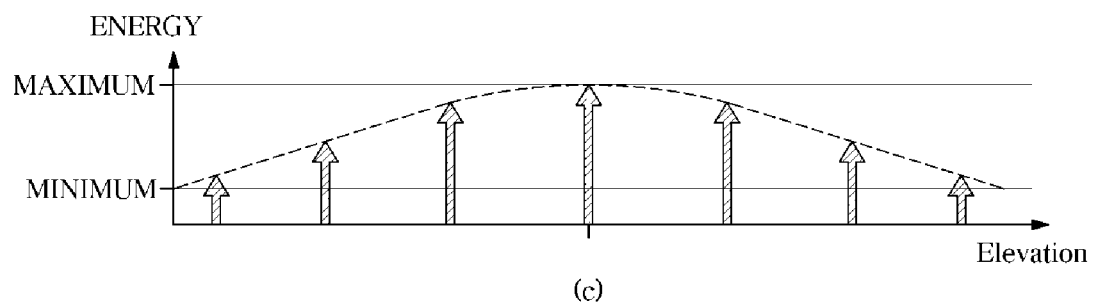
Figure 7:
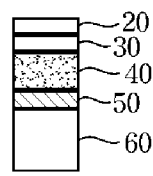
Figure 7:
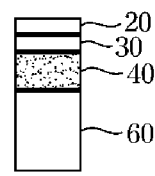
Figure 7:
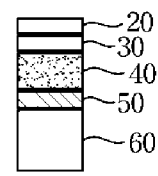
Figure 8:
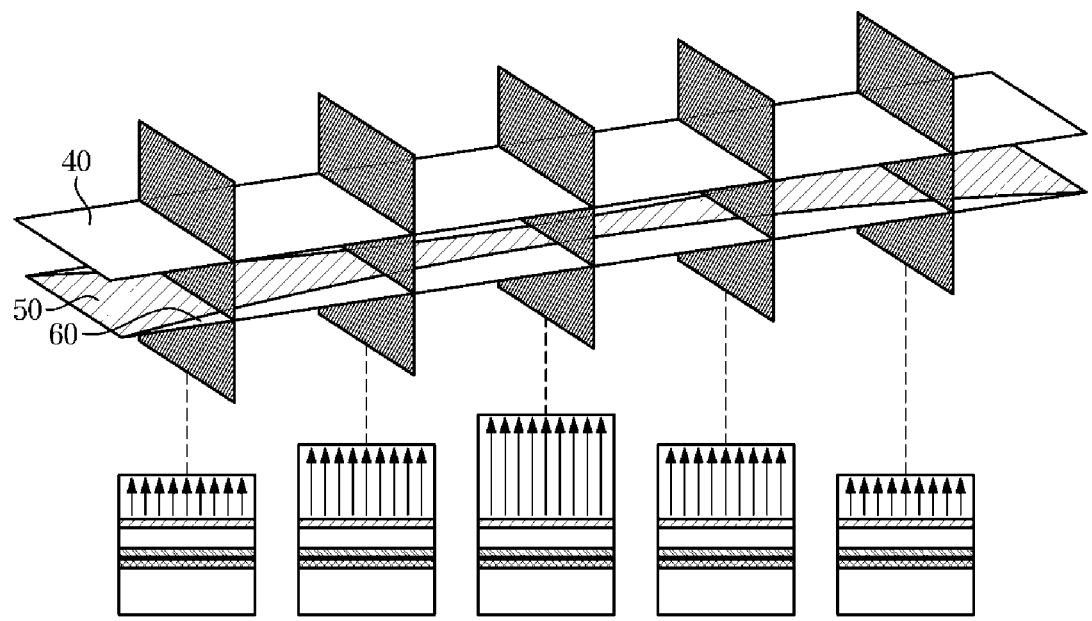
Figure 9:
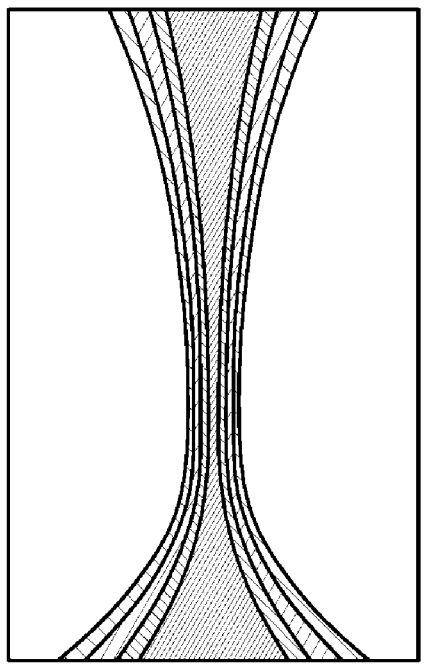
FIG. 9 is a view illustrating a comparison between a shape of an ultrasonic signal emitted from an ultrasonic probe according to an embodiment of the disclosure and the shape of the ultrasonic signal emitted from the ultrasonic probe according to a related art.
Figure 9:
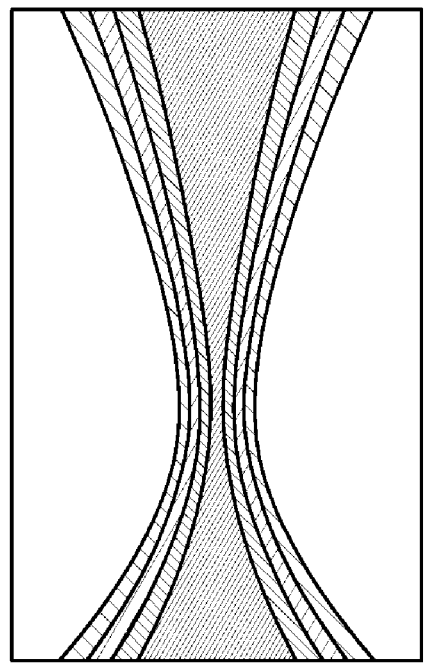

FIG. 5 is a view illustrating a laminated structure of an acoustic element of an ultrasonic probe according to an embodiment of the disclosure, FIG. 6 is an exploded perspective view illustrating an acoustic element of an ultrasonic probe according to an embodiment of the disclosure, FIGS. 7 and 8 are views illustrating the magnitude of the acoustic energy radiated differently depending on a position of a connection part according to an embodiment of the disclosure, and FIG. 9 is a view illustrating a comparison between a shape of an ultrasonic signal emitted from an ultrasonic probe according to an embodiment of the disclosure and the shape of the ultrasonic signal emitted from the ultrasonic probe according to a related art.

Referring to FIGS. 5 and 6, the ultrasonic probe 100 according to the disclosure may include a piezoelectric layer 40, a matching layer 30 disposed at the upper portion of the piezoelectric layer 40, an acoustic lens 20 disposed at the upper portion of the matching layer 30, an absorbing layer 60 disposed at the lower portion of the piezoelectric layer 40, a connection portion 50 disposed between the piezoelectric layer 40 and the absorbing layer 60, and the like.

The features of the acoustic lens 20, the matching layer 30, the piezoelectric layer 40 and the absorbing layer 60, except for the connection part 50, are the same as those described in FIG. 4, and the structure and features of the connection part 50 are described. For example, the matching layer 30 may be formed a single layer, or formed of a first matching layer 30*a* and a second matching layer 30*b*.

The connection part 50 may also be referred to as an interconnection layer according to its designation and may be disposed between the piezoelectric layer 40 and the absorbing layer 60 but may also be disposed between the piezoelectric layer 40 and the matching layer 30.

Also, the connection part 50 may be electrically connected to the piezoelectric layer 40, and may include at least one flexible printed circuit board (PCB) or a conductive material depending on the purpose of use.

Since the piezoelectric layer 40 of the ultrasonic probe 100 is disposed at the upper portion of the connection part 50, the piezoelectric layer 40 vibrates due to mass loading of the connection part 50 and radiates the acoustic signal to the outside. The magnitude of energy radiated from the piezoelectric layer 40 may differ depending on the size, material, and thickness of the connection part 50.

However, in the case of the ultrasonic probe according to the related art, the connection part model has the same model as other materials laminated on the acoustic element, for example, a rectangular model, and the acoustic energy radiated from the center or the side direction of the ultrasonic probe, respectively. Therefore, there is a problem that the directivity of the ultrasonic signal decreases and the side lobe of the ultrasonic probe increases.

In the case of the ultrasonic probe 100 according to the disclosure, as illustrated in FIG. 6, a part of the connection part 50 is deformed, so that the mass loading effect of the connection part 50 applied to the piezoelectric layer 40 differs depending on the position of the piezoelectric layer 40, and the magnitude of energy radiated from the piezoelectric layer 40 may be also radiated differently depending on the position.

FIG. 7 is a view for describing this. FIG. 7A is a view illustrating the shape of the connection part 50 according to an embodiment of the disclosure, FIG. 7B is a graph illustrating an area ratio of the connection part 50 according to an elevation position, FIG. 7C is a graph illustrating the magnitude of energy radiated according to the elevation position of the ultrasonic probe 100, and FIG. 7D is a perspective view of the ultrasonic probe 100 viewed from the side when the connection part 50 illustrated in FIG. 7A is mounted on the ultrasonic probe 100.

Referring to FIG. 7A, the width of the connection part 50 is wide at the side of the connection part 50 and decreases at the center of the connection part 50, and FIG. 7B is a graph illustrating this shape.

As illustrated in FIG. 7C, when the connection part 50 has the shape as illustrated in FIG. 7A, the magnitude of energy radiated from the ultrasonic probe 100 has different characteristics depending on its position.

In other words, since the connection part 50 is electrically connected to the piezoelectric layer 40 and may include the at least one flexible PCB, the magnitude of the acoustic energy radiated from the ultrasonic probe 100 depends on the presence or absence of the flexible PCB.

In the case of adopting the structure illustrated in FIG. 7A, the magnitude of the acoustic energy radiated from the ultrasonic probe 100 is small in the side where the connection part 50 has a relatively large width. However, the magnitude of the acoustic energy radiated from the ultrasonic probe 100 is large in the center where the connection part 50 has the relatively large width.

Therefore, the magnitude of the acoustic energy radiated from the center of the ultrasonic probe 100 is greater than the magnitude of the energy radiated from the side, so that the directivity of the ultrasonic signal may be improved.

That is, a pattern of the ultrasonic signal of the ultrasonic probe according to the related art tends to spread sideways as illustrated in FIG. 9B, but the pattern of the ultrasonic signal of the ultrasonic probe 100 according to the disclosure is relatively centered as illustrated in FIG. 9A, so that the directivity of the ultrasonic signal may be improved as compared with the related art.

Since the magnitude of the acoustic signal radiated from the side is smaller than the magnitude of the acoustic signal radiated from the center, the side lobe radiated from the side of the ultrasonic probe 100 may be decreased, and a focus zone of the ultrasonic signal may be widened at the same time.

In addition, an apodization effect that can suppress the overlap between adjacent phases may be obtained by using the difference between the acoustic energy radiated from the center of the ultrasonic probe 100 and the acoustic energy radiated from the side.

Figure 10:
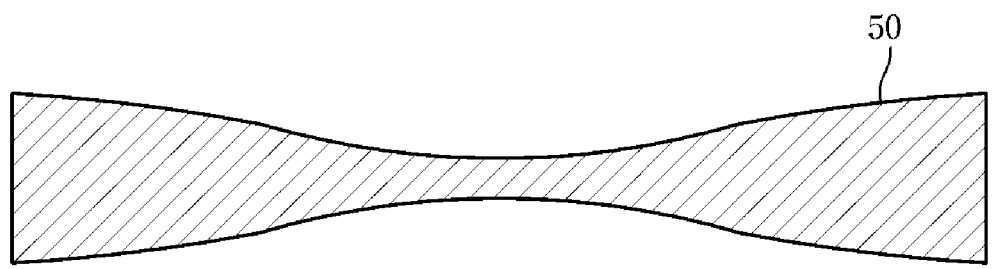
FIG. 10 is a view illustrating various shapes of connection parts according to an embodiment of the disclosure.
Figure 10:
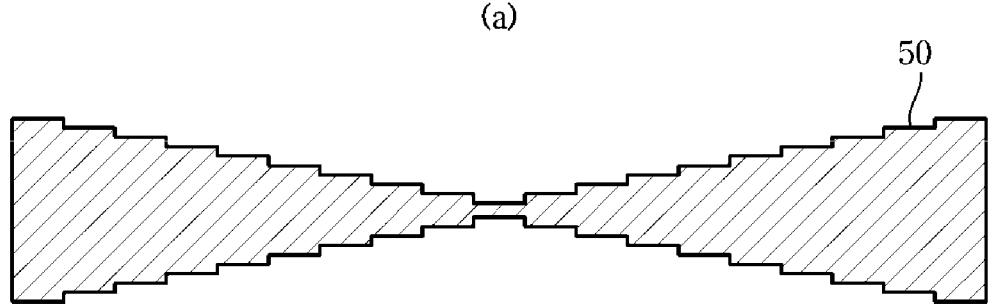
Figure 10:
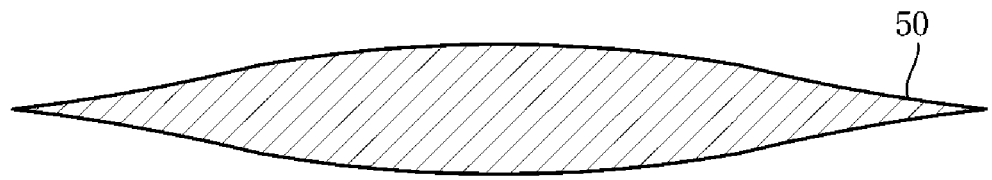
Figure 10:
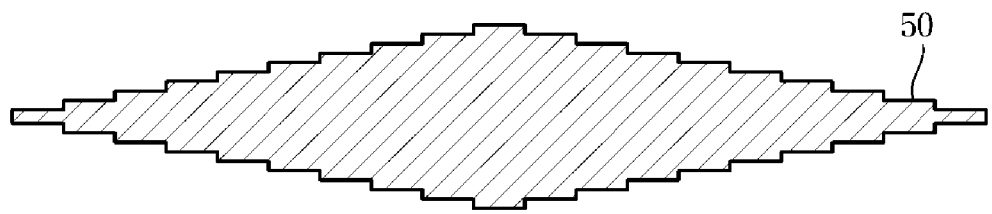

FIG. 10 is a view illustrating various shapes of connection parts according to an embodiment of the disclosure.

In the exemplary embodiment illustrated in FIG. 6, the model of the connection part 50 is illustrated symmetrically with a concave shape, but the disclosure is not limited thereto. As illustrated in FIG. 10, the connection part 50 may have various shapes.

That is, a rectangle rather than a curved line may be formed as illustrated in FIGS. 10B and 10D, and a convex shape opposite to FIG. 10A may be formed as illustrated in FIG. 10C. In this case, since the shape of the connection part 50 varies, the magnitude of the energy radiated from the ultrasonic probe 100 may also vary depending on the position, as described above.

Therefore, it is possible to produce an ultrasonic probe 100 suitable for the purpose by modifying the model of the connection part 50 according to the use environment and purpose of the ultrasonic probe 100.

In addition, the model of the connection part 50 may have various shapes, as illustrated in FIG. 10. Depending on the purpose of use, the part of the connection part 50 may be deformed, and one side of the connection part 50 may have the shape of the curved line or an inwardly connected line.

The outer circumferential surface of the connection part 50 may symmetrically form the convex or concave shape. The width of the connection part 50 has a different width from one side of the connection part 50 to the center of the connection part 50. The width of the connection part 50 may have of linearly increasing shape from one side of the connection part 50 to the center of the connection part 50 or increasing in a curved shape. The width of the connection part 50 may have of linearly decreasing shape from one side of the connection part 50 to the center of the connection part 50 or decreasing in the curved shape.

Also, the connection part 50 may have the shape of the part of the connection part 50 being deformed so as to the magnitude of the acoustic signal radiated for its purpose of use linearly increases or decreases from one side of the connection part 50 or to increase or decrease in the curved shape, and may have the shape of a circle, an ellipse, or a rhombus.

Figure 11:
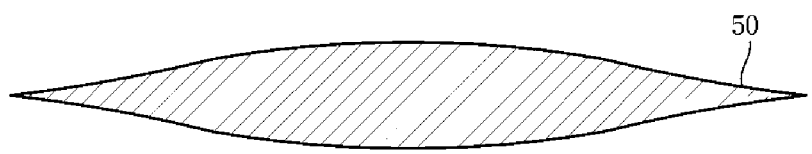
FIG. 11 is a view illustrating the magnitude of energy radiated depending on a position of a connection part according to an embodiment of the disclosure.
Figure 11:
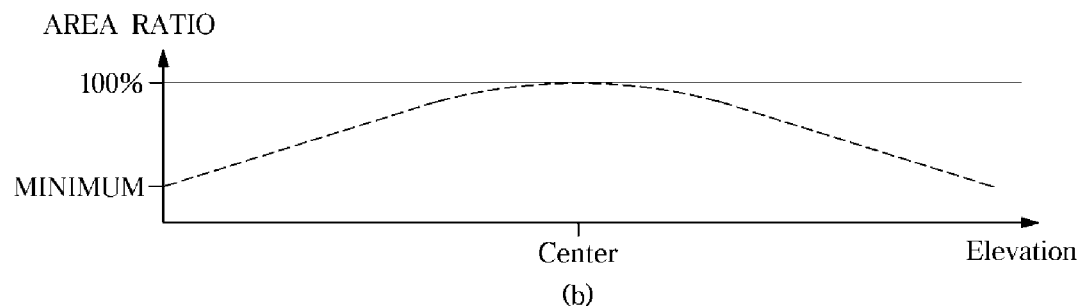
Figure 11:
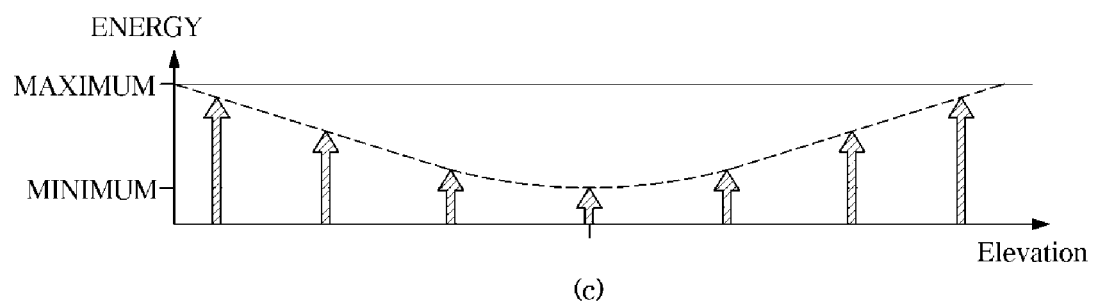
Figure 11:
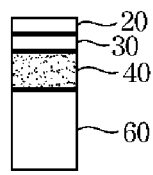
Figure 11:
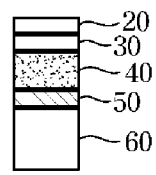
Figure 11:
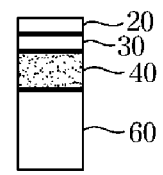

FIG. 11 is a view illustrating the magnitude of radiant energy emitted according to the position when the connection part 50 forms the shape of FIG. 10C.

Referring to FIG. 11A, the width of the connection part 50 is small on the side, but the width of the connection part 50 increases toward the center, and the width of the connection part 50 decreases toward the other side. FIG. 11B is a view illustrating such the shape using the graph.

When the connection part 50 has the shape as illustrated in FIG. 11A, the magnitude of energy radiated from the ultrasonic probe 100 may vary as illustrated in FIG. 11C.

That is, the connection part 50 may be electrically connected to the piezoelectric layer 40 and may include the flexible PCB, so that the magnitude of the acoustic energy radiated from the ultrasonic probe 100 is radiated differently depending on the presence or absence of the flexible PCB.

Therefore, when the connection part 50 has the structure as illustrated in FIG. 11A, the magnitude of the acoustic energy radiated from the ultrasonic probe 100 is large in the side where the width of the connection part 50 is relatively large, but the smaller the relative width of the connection part 50 is toward the center, the magnitude of energy radiated from the ultrasonic probe 100 is decreased. Therefore, the utilization of the ultrasonic probe 100 may be enhanced according to the purpose by using such characteristics.

Figure 12:
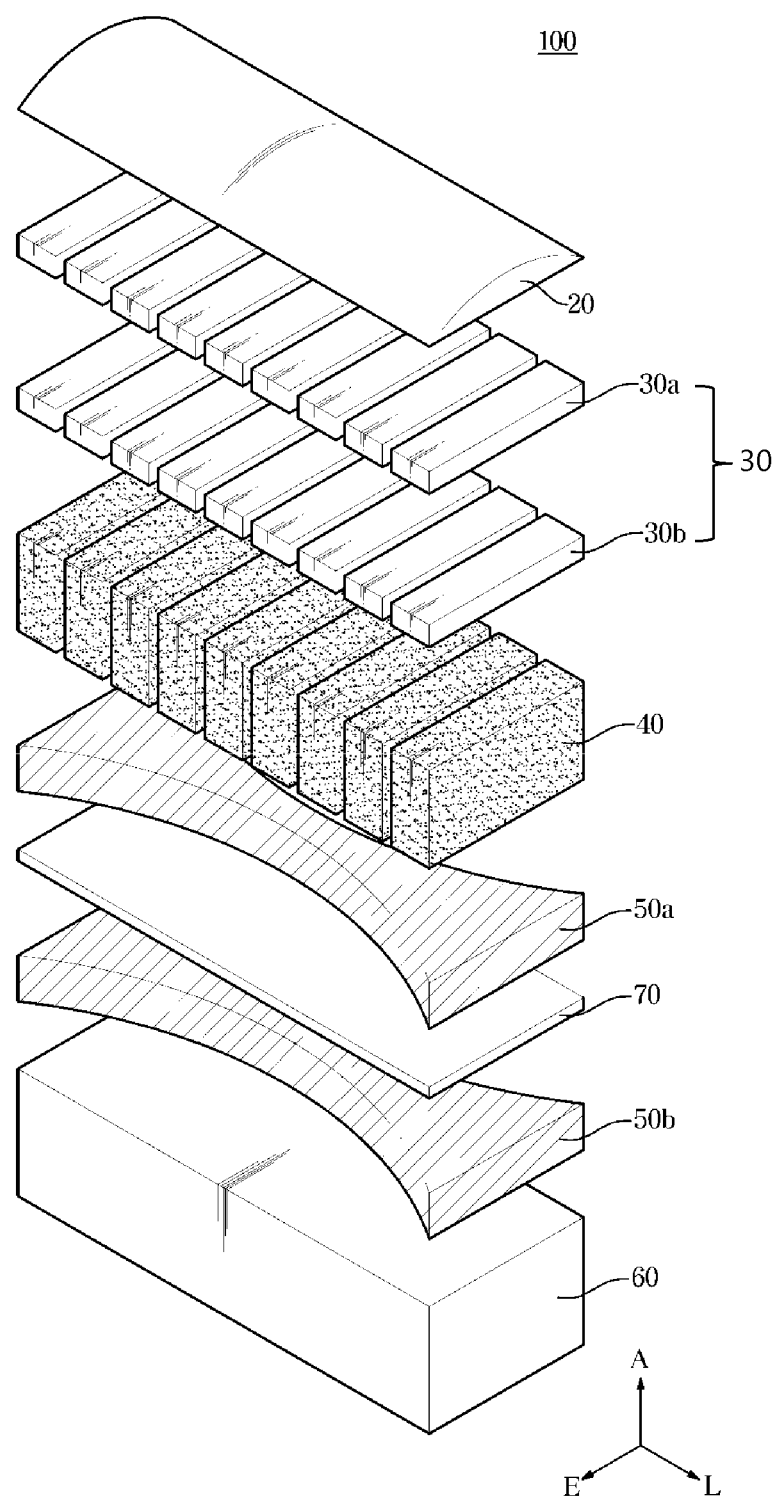
FIG. 12 is a view illustrating a laminated structure of an acoustic element of an ultrasonic probe according to another embodiment of the disclosure.
Figure 13:
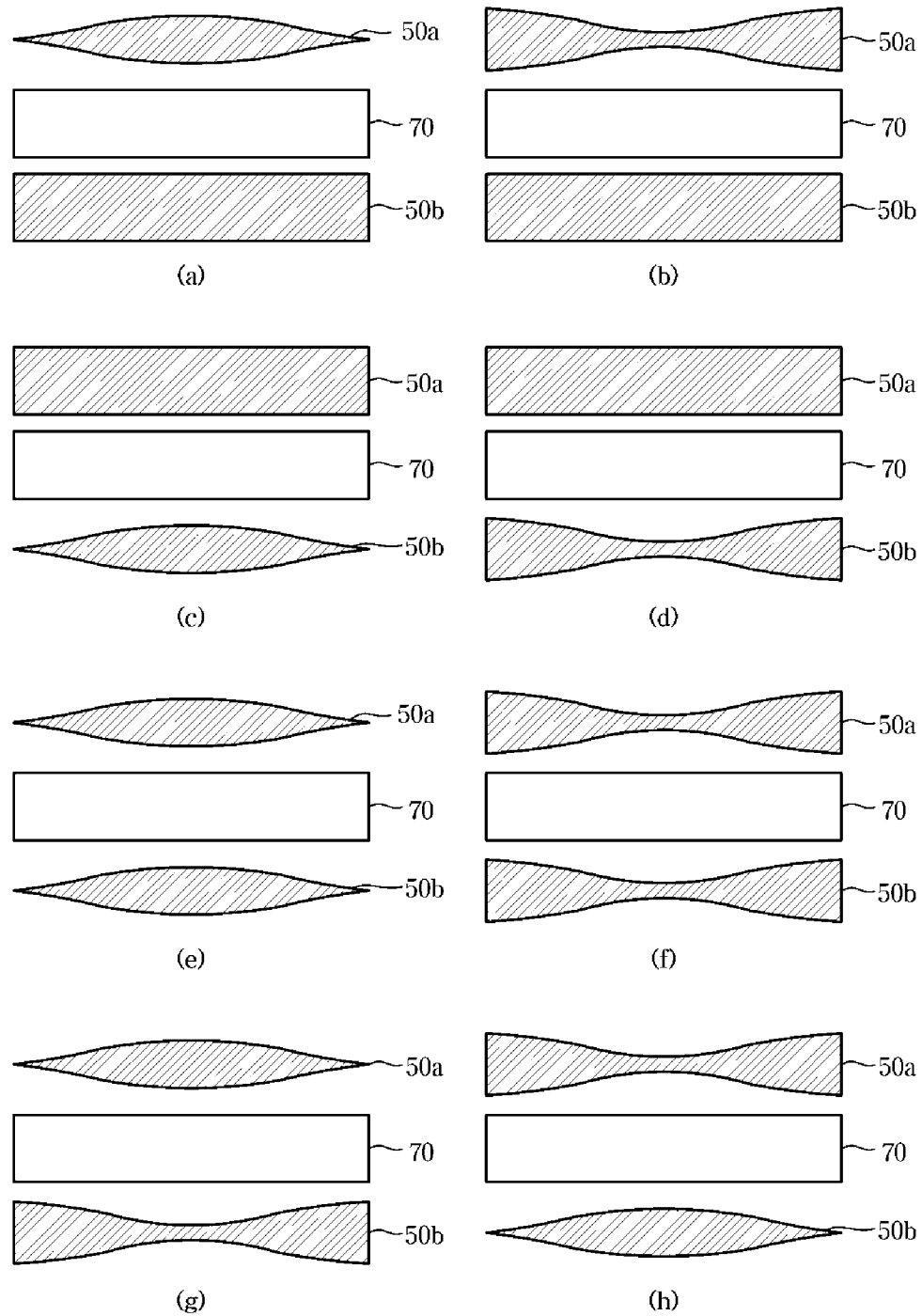
FIG. 13 is a view illustrating various shapes of connection parts according to another embodiment of the disclosure.
Figure 14:
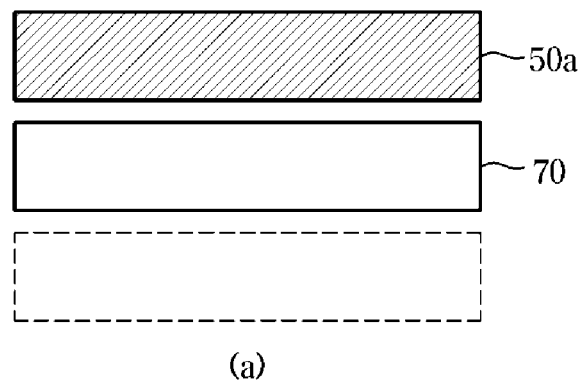
FIG. 14 is a view illustrating various shapes of connection parts according to another embodiment of the disclosure.
Figure 14:
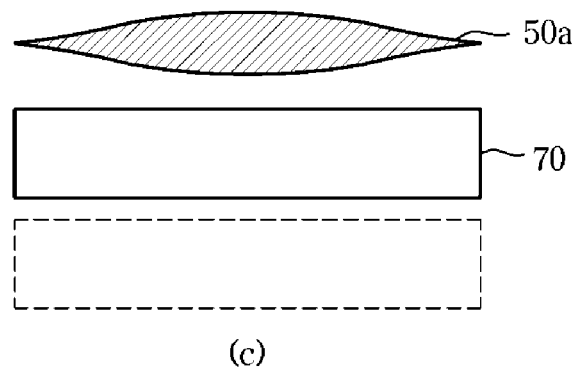
Figure 14:
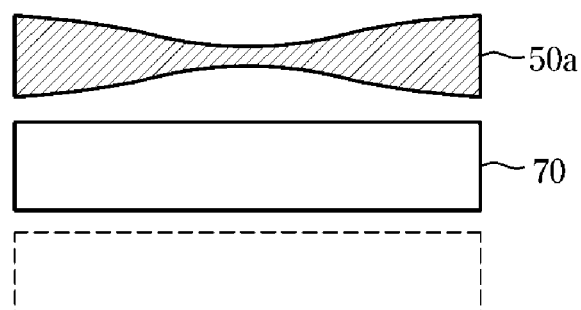

FIG. 12 is a view illustrating a laminated structure of an acoustic element of an ultrasonic probe according to another embodiment of the disclosure, and FIGS. 13 and 14 are views illustrating various shapes of connection parts according to another embodiment of the disclosure.

Referring to FIG. 12, the ultrasonic probe 100 according to another embodiment of the disclosure may include the piezoelectric layer 40, the matching layer 30 disposed at the upper portion of the piezoelectric layer 40, the acoustic lens 20 disposed at the upper portion of the matching layer 30, the absorbing layer 60 disposed at the lower portion of the piezoelectric layer 40, and a plurality of connection portions 50a and 50b disposed between the piezoelectric layer 40 and the absorbing layer 60. An insulating layer 70 may be included between the first connection part 50a and the second connection part 50b. The acoustic lens 20, the matching layer 30, the piezoelectric layer 40, and the absorbing layer 60 are the same as those described in FIG. 5.

The ultrasonic probe 100 illustrated in FIG. 12 may include the two connection parts 50a and 50b. As illustrated in FIG. 13, the two connection parts 50a and 50b may have various shapes depending on the purpose of use and the manufacturing environment of the ultrasonic probe 100.

That is, only the first connection part 50a may be the convex or concave shape (see FIGS. 13A and 13B), and only the second connection part 50b may be the convex or concave shape (FIGS. 13C and 13D). In addition, both the first connection part 50a and the second connection part 50b may be the convex or concave shape (FIGS. 13E and 13F). The first connection part 50a may be the convex shape and the second connection part 50b may be the concave shape (FIG. 13G). The first connection part 50a may be the concave shape and the second connection part 50b may be the convex shape (FIG. 13H).

The shape of the first connection part 50a and the second connection part 50b is not limited to the shape illustrated in FIG. 13, and may have various shapes described in FIG. 10. Although the two connection parts 50a and 50b are illustrated in FIG. 12, the disclosure is not limited thereto and may include two or more plural connection parts 50.

As illustrated in FIG. 14, the second connection part 50b does not exist and only the first connection part 50a and the insulating layer 70 may be disposed between the piezoelectric layer 40 and the absorbing layer 60. The first connection part 50a may be configured in various shapes such as the rectangular shape (see FIG. 14A), the convex shape (see FIG. 14B), the concave shape (FIG. 14C), and the like.

The features and effects of the disclosure have been described through various embodiments of the disclosure.

In the case of the ultrasonic probe according to the related art, the materials constituting the acoustic elements are all laminated in the same shape, and the magnitude of energy radiated from the ultrasonic probe is constant in all surfaces. Therefore, there is a problem that the directivity of the ultrasonic signal is lowered and the side lobe is increased However, in the case of the ultrasonic probe 100 according to the disclosure, since the shape of the connection part 50 is partially deformed, the magnitude of the acoustic energy radiated from the ultrasonic probe 100 is larger than the acoustic energy radiated from the side, so that the directivity of the ultrasonic signal is improved and the side lobe of the ultrasonic probe 100 is decreased.

Although the disclosure is described with reference to some embodiments as described above and accompanying drawings, it will be apparent to those ordinary skilled in the art that various modifications and changes can be made to the embodiments. For example, the aforementioned method may be performed in different order, and/or the aforementioned systems, structures, devices, circuits, etc., may be combined in different combinations from what is described above, and/or replaced or substituted by other components or equivalents thereof, to obtain appropriate results. Therefore, other implementations, other embodiments, and equivalents thereof may fall within the following claims.

The invention claimed is:

1. An ultrasonic probe comprising:
   a piezoelectric layer;
   an absorbing layer disposed at a lower portion of the piezoelectric layer, configured to absorb an acoustic signal; and
   a connection part disposed between the piezoelectric layer and the absorbing layer,
   wherein the connection part is configured to deform partially so that a magnitude of an acoustic signal of a plurality of acoustic signals radiated from the piezoelectric layer linearly increases or decreases, or the magnitude of the acoustic signal of the plurality of acoustic signals radiated from the piezoelectric layer increases or decreases in a curved shape from one side of the connection part to a center of the connection part, and
   wherein a width of the connection part decreases from both sides of the connection part toward the center of the connection part along an elevation direction, and a width of the both sides of the connection part is greater than a width of the center of the connection part.

2. The ultrasonic probe according to claim 1, wherein the connection part is configured to have a symmetrical shape with respect to a center line of the connection part.

3. The ultrasonic probe according to claim 1, wherein at least the one side of the connection part is configured to have the curved shape.

4. The ultrasonic probe according to claim 1, wherein an outer circumferential surface of the connection part is configured to have a concave shape symmetrically.

5. The ultrasonic probe according to claim 1, wherein the width of the connection part is configured to linearly decrease or decrease in the curved shape from the both sides of the connection part to the center of the connection part.

6. The ultrasonic probe according to claim 1, wherein the connection part comprises a plurality of connection layers, and an insulating layer is disposed between the plurality of connection layers.

7. The ultrasonic probe according to claim 1, wherein the connection part comprises a first connection part and a second connection part, and an insulating layer is disposed between the first connection part and the second connection part.

8. The ultrasonic probe according to claim 7, wherein an outer circumferential surface of the first connection part is configured to have a concave shape symmetrically.

9. The ultrasonic probe according to claim 7, wherein an outer circumferential surface of the second connection part is configured to have a concave shape symmetrically.

10. The ultrasonic probe according to claim 1, wherein the width of the connection part indicates a dimension of the connection part in a width direction different from a stacking direction of the piezoelectric layer, the connection part, and the absorbing layer and the elevation direction,
   the width of the both sides of the connection part indicates a dimension of the both sides of the connection part in the width direction, and
   the width of the center of the connection part indicates a dimension of the center of the connection part in the width direction.

* * * * *